United States Patent [19]

Lee et al.

[11] Patent Number: 4,921,473
[45] Date of Patent: May 1, 1990

[54] MULTICOMPONENT FLUID SEPARATION AND IRRADIATION SYSTEM

[75] Inventors: Kyu H. Lee, Bryn Mawr; Livingston B. Morris, Devon, both of Pa.

[73] Assignee: Therakos, Inc., Westchester, Pa.

[21] Appl. No.: 305,339

[22] Filed: Feb. 2, 1989

[51] Int. Cl.[5] .................... B04B 11/00; B04B 5/10
[52] U.S. Cl. ................................ 494/27; 422/44; 422/72; 494/41; 494/60
[58] Field of Search .............. 494/85, 10, 27, 35, 494/36, 37, 41, 60; 604/6, 4, 5; 422/44, 72; 210/781, 782

[56] References Cited

U.S. PATENT DOCUMENTS

| | | |
|---|---|---|
| 4,140,268 | 2/1979 | Lacour .............................. 494/41 |
| 4,300,717 | 11/1981 | Latham ............................ 494/41 |
| 4,321,919 | 3/1982 | Edelson . |
| 4,398,906 | 8/1983 | Edelson . |
| 4,428,744 | 1/1984 | Edelson . |
| 4,464,166 | 8/1984 | Edelson . |
| 4,573,960 | 3/1986 | Goss . |
| 4,573,961 | 3/1986 | King . |
| 4,613,322 | 9/1986 | Edelson . |
| 4,726,949 | 2/1988 | Miripol et al. . |
| 4,737,140 | 4/1988 | Lee et al. . |

FOREIGN PATENT DOCUMENTS

88/00295 8/1988 PCT Int'l Appl. .

Primary Examiner—Robert W. Jenkins
Attorney, Agent, or Firm—Donal B. Tobin

[57] ABSTRACT

A multicomponent fluid separation and irradiation system is described containing a centrifuge drum and a source of radiant energy located within the drum. In a first embodiment a disposable rigid separation/irradiation chamber is provided with a cylindrical outer compartment located within the drum and opposing the radiant energy source. Whole blood is supplied to the chamber through a dynamic seal located at the center of the chamber. As the chamber is rotated, blood is separated so that energy from the source passes through the inner wall of the chamber and the separated plasma layer to irradiate the buffy coat layer. In a second embodiment, one or both of the walls of the outer compartment of the chamber are flexible so that the chamber will expand as blood is pumped in and will collapse as blood is pumped out.

33 Claims, 6 Drawing Sheets

MULTICOMPONENT FLUID SEPARATION AND IRRADIATION SYSTEM

This invention relates to systems for separating and irradiating multicomponent fluids and, in particular, to the use of such systems in the field of treating cells with photoactivatable compounds by radiation, which activates the compounds to effect cellular change.

Numerous human disease states of the blood respond favorably to the treatment of selected blood components by visible or ultraviolet light irradiation. Such treatment may be effective to eliminate immunogenicity in cells, inactivate or kill selected cells, inactivate viruses or bacteria, or activate desirable immune responses. Certain forms of treatment with light irradiation may be effective without the introduction of outside agents or compounds, while others may involve the introduction of specific agents or catalysts. Among the latter treatment techniques is the use of photoactivatable agents to regulate the population of leukocytes. It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects in patients including the functional impairment of bodily organs, leukocyte mediated autoimmune diseases and leukemia related disorders many of which often ultimately result in fatality.

U.S. Patent Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of ultraviolet (U.V.) radiation. It is believed that covalent bonding results between the psoralen and the lymphocyte nucleic acid thereby effecting metabolic inhibition of the treated cells. Following extracorporeal irradiation, the cells are returned to the patient where they are thought to be cleared by natural processes but at an accelerated pace believed attributable to disruption of membrane integrity, alteration of DNA within the cell, or like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum may occur. For instance, it may be preferable to treat some disease states with light in the ultraviolet spectrum of 280 to 320 nanometers, referred to as the U.V.B. spectrum. Suitable selection of radiation sources may be expected to increase treatment efficiency and is contemplated as an obvious optimization procedure for use with the invention disclosed herein.

In initial implementations of the Edelson methods whole blood was treated in vitro using devices such as flasks, filtration columns, spectrophotometer cuvettes, and petri dishes. The blood sample to be irradiated was added to the containers and the containers placed adjacent to the radiation source. Such systems were characterized by difficulty in providing the necessary safeguards intrinsically necessary where patient bodily fluids are concerned, particularly since these fluids must be returned to the patient, thereby necessitating strict avoidance of contamination. Further, such methods tend to be volume limited, are characterized by many mechanical manipulations and are generally unacceptable from a clinical and regulatory viewpoint.

U.S. Pat. No. 4,573,960 describes an advance made in these initial implementation techniques by Taylor. Taylor describes a practical device for coupling the radiation provided by commercially available light sources, such as so-called "black-light" fluorescent tubes, to cells for treatment by Edelson's photoactivated drug methods. In summary, the disposable cassette described by Taylor comprises a plurality of fluorescent tube-like light sources such as the U.V.A. emitting Sylvania F8T5/BLB bulb, which are individually, coaxially mounted in tubes of larger diameter which are, in turn, coaxially mounted in sealing arrangement within second outer tubes of even larger diameter, thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are serially interconnected between inlets and outlets of adjacent members to provide for serpentine flow of cells through each outer cavity. Thus, continuous flow of the cells through the plurality of cavities surrounding the centrally disposed radiation sources facilitates thorough treatment of the cells.

To be fully practical, however, the Taylor device requires a clinically acceptable instrument to house the device and to provide the cells to be treated in an appropriate form. Such an instrument and a method for its use are described in the aforementioned U.S. Patent 4,573,960. The method there described for extracorporeally photoactivating a photoactivatable reagent in contact with blood cells comprises the steps of collecting and separating on a continuous basis blood from a patient while the patient is connected to the instrument, returning undesired blood portions obtained during separation, and disconnecting the patient from the treatment system while the desired portion is photoactivatably treated, whereafter the treated cells are returned to the patient. Thus, the instrument and method of this patent broadly maximizes a patient's safety and optimizes the various aspects of such photoactivation treatment by breaking the entire procedure down into three phases or modes. In the first mode the instrument collects and separates blood on a continuous basis as it is withdrawn from the patient and returns unwanted portions to the patient, all of which are accomplished while the patient remains connected to the apparatus. Thereafter, prior to energizing the irradiation sources for photoactivating the photoactivatable reagent in contact with the desired blood portion, the patient may be disconnected from the instrument while irradiation and photoactivation are performed on the separated component of the blood during the second mode. Following photoactivation the treated cells may then be facilely returned to the patient during a third mode, utilizing a variety of techniques, the preferred being a simple drip chamber gravity feed infusion line.

While the foregoing instrument and method provide a system which has met clinical and regulatory standards, it is desirable to provide the system with even greater clinical and operational efficiency. It would be desirable, for instance, to combine the first and second modes of the prior method, whereby the desired blood component is photoactivatably treated during separation of the blood components. While improving efficiency and reducing system complexity, such an improvement would also eliminate the blood tubing set, valves, container, and tubular or flat plate cassettes required for the separate irradiation mode of operation in the prior apparatus described in the aforementioned U.S. Pat. No. 4,573,960 and in U.S. Pat. No. 4,737,140 (Lee et al.) In such an improved arrangement, the dynamic operating variables of the separation process could be used to controllably irradiate the desired blood component while minimizing unnecessary irradiation of other components of the blood. Furthermore, the necessary remixing of the separated blood components may be performed at the conclusion of the irradiation treatment by the same apparatus that initially separates the blood components, thereby obviating the intervening step of returning only unwanted components to the patient.

In accordance with the principles of the present invention, a multicomponent fluid separation and irradiation apparatus is provided which may be advantageously utilized to separate and irradiate desired components of blood. The apparatus includes a rotatable separation chamber having a sealed outer compartment. The inner wall of the compartment is transparent to the desired wavelength of a light source located in opposition to the inner wall. The fluid to be separated and irradiated is introduced into the compartment through a passageway passing through a dynamic seal axially aligned with the rotatable chamber. Following passage through the dynamic seal, the fluid is conducted through a radially aligned passageway to the sealed outer compartment of the separation chamber. As the separation chamber rotates the fluid in the outer compartment is centrifugally separated and its inner layer or layers are selectively exposed to the light source opposing the inner wall of the chamber. Following separation and irradiation the fluid components are remixed within the separation chamber and withdrawn through the entry passageways.

In a first embodiment of the present invention the radial passageway is located at the bottom of the separation chamber. In a second embodiment the radial passageway is located at the top of the separation chamber and is connected to a further passageway in the separation chamber leading to the bottom of the chamber. Both embodiments facilitate efficient withdrawal of the treated fluid following separation and irradiation.

Figure 1:
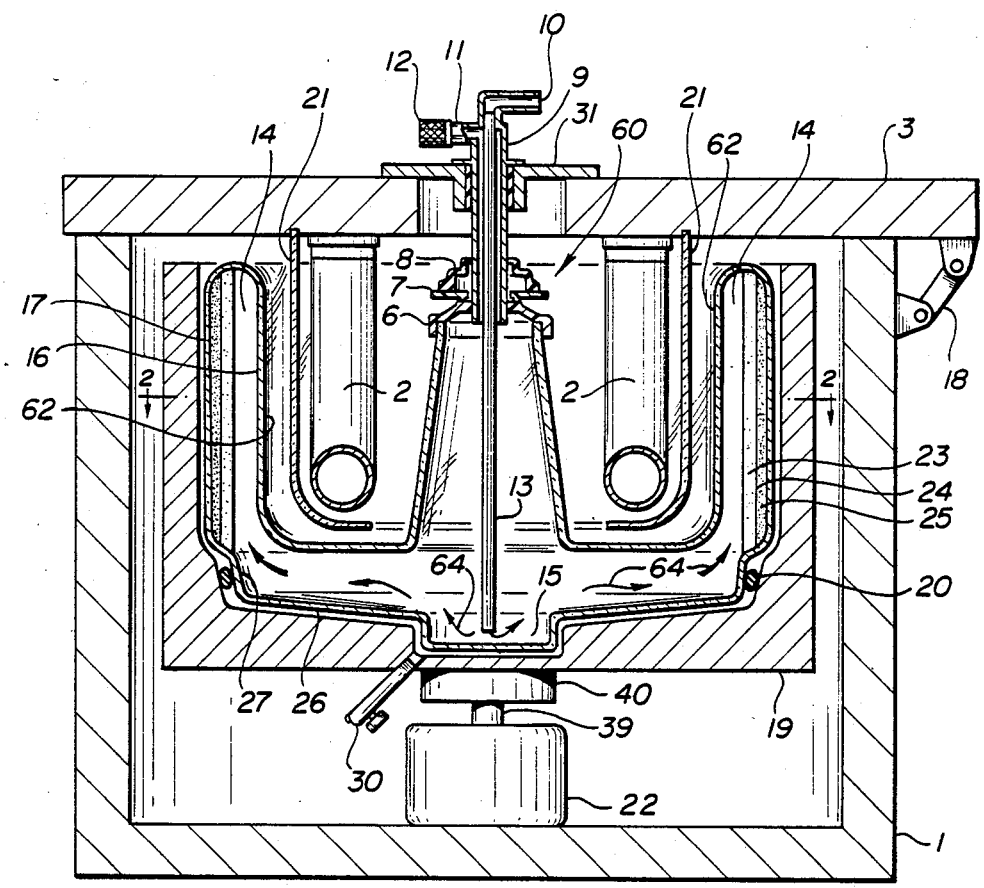
FIG. 1 illustrates in a partially cross-sectional view a first embodiment of a multicomponent fluid separation and irradiation system constructed in accordance with the principles of the present invention.
Figure 2:
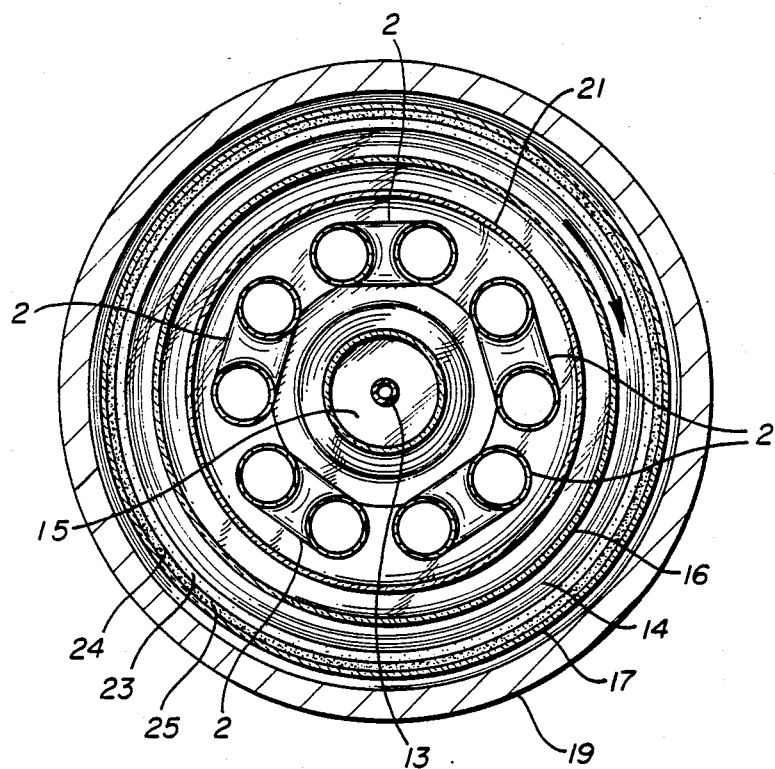
FIG. 2 is a plan cross-sectional view of the system of FIG. 1.

Referring first to FIG. 1, a whole blood separation and irradiation device constructed in accordance with the principles of the present invention is shown. The device comprises a stationary housing 1 and cover 3 which encloses a rotatable separation/irradiation chamber 14. Depending from the stationary centrifuge cover is a light source in the form of five U-shaped U.V. bulbs 2. The bulbs are arranged in a generally circular configuration around the inside of the separation/irradiation chamber of the device as shown in the plan cross-sectional view of FIG. 2. The bulbs are shielded about their outer perimeter by a protective bulb cover 21, which also is attached to the cover 3.

The stationary and rotatable sections of the device are joined by a rotary seal 60 at the axial center of the device The rotary seal 60 includes an upper, nonrotating disk-shaped component 7 and a lower, rotating disk-shaped component 6. The nonrotating component 7 is attached to a central shaft 9 of the device by an elastic member 8. The central shaft in turn passes through and is attached to the cover 3 by a clamp 31. The elastic member 8 urges the nonrotating component 7 downward so that the annular contacting surface of the component 7 is in contact with the upper surface of the rotating component 6 of the seal, thereby establishing a dynamic seal as the rotatable section of the device is rotated. The rotary seal is of the type described in U.S. Pat. No. 4,300,717.

Extending through the shaft 9 from above the cover 3 to the bottom of the separation/irradiation chamber is a feed tube 13. Axially extending from the shaft 9 is an air outlet port 11, the distal end of which is sealed with a microbial filter 12. Alternatively, the distal end of the air outlet port may be connected to a sterile empty bag. As the separation/irradiation chamber 14 is filled with whole blood, displaced air passes through the passageway between the feed tube 13 and the inner wall of the shaft 9. The air is then vented out through the filter 12 or into the empty bag The distal end 10 of the feed tube 13 may be fitted with a connection to connect the tube to a blood supply line (not shown).

The rotatable section of the device includes a continuously sealed separation/irradiation chamber 14 having a cylindrical outer compartment 62. The outer compartment 62 has an outer wall 17 and an inner wall 16 which opposes the light source 2. The inner wall 16 is made of a material transparent to a wavelength of the light source For example, acrylic plastics, polyethylene, polypropylene, polyvinylchloride, pyrex glass, and silica are transparent to ultraviolet and visible light. The separation/irradiation chamber 14 is seated inside a chuck 19, and is sealed therein by an O-ring 20. The chuck 19 is connected by a coupling 40 to the shaft 39 of a motor 22 in the bottom of the housing that rotates the chuck at the desired speed. Centrifugal forces will thus be developed in the separation/irradiation chamber 14 and its outer compartment 62 as the chamber is rotated about the light source 2. The chamber 14 remains sealed during rotation by the rotary seal 60. A drain tube 30 allows drainage of cleaning and other fluids from the chuck 19 by opening a stopcock on the drain tube.

The cover 3 is connected to the housing 1 by a hinge 18. The hinge desirably articulates so that when the clamp 31 is unclamped and opened about the shaft 9 the cover can be lifted and will clear the shaft 9 and the air outlet port 11 without interference.

In operation, the motor is energized to rotate the separation/irradiation chamber 14 for the generation of centrifugal forces within the chamber. A desirable range of the centrifugal speed is 1000–6000 RPM. A blood supply line is connected to the distal end 10 of the feed tube 13 and whole blood treated with a photoactivatable compound and preferably an anticoagulant is supplied to the tube by a blood pump or gravity feed. As the blood enters the system the air displaced by the volume of blood is vented out through the air outlet port 11 and microbial filter 12 or into a sterile empty bag. The whole blood passes down the tube to the recessed blood collection well 15 at the bottom of the separation/irradiation chamber 14. The centrifugal forces of the rotating chamber push the blood out of the well 15 and up the sloped bottom 26 of the chamber to the outer compartment 62 of the chamber. A step 27 is formed at the junction of the bottom of the chamber and the outer compartment 62 whereby substantially all of the blood will be elevated above the bottom of the chamber and into the compartment 62 without contacting the inner wall 16 of the chamber. The rotating chamber forces the blood against the outer wall 17 of the separation/irradiation chamber where cell separation occurs in accordance with the sedimentation rates of individual blood components. This centrifugal separation will result in the development of a layer 25 of red blood cells in contact with the outer wall 17 of the chamber. The innermost separated layer comprises a plasma layer 23, and between the red blood cell layer and the plasma layer is a thin lYmphocyte enriched layer 24, referred to herein as a buffy coat layer. Thus the red blood cells, which would otherwise act to shield other blood components from U.V. light, are located outside the lymphocyte enriched buffy coat layer. The composition of whole blood, and hence the relative thicknesses of the separated layers, is approximately 45% red blood cells, 55% plasma, and 0.1% buffy coat.

The sedimentation rate of lymphocytes is lower than that of other white blood cells in the buffy coat 24. Thus, the lymphocytes are highly concentrated in the side of the buffy coat which opposes the plasma layer 23. U.V. light from the light source 2 will therefore pass through the protective bulb cover 21, the inner wall 16 of the separation/irradiation chamber, and the plasma layer 23 to irradiate the lymphocytes in the buffy coat 24, a sequence shown in the view of FIG. 2. Since the rotational forces in the chamber 14 will establish buffy coat and plasma layers of uniform thickness by reason of the vertical wall 17 of the chamber, the lymphocytes will be uniformly irradiated by the light source. By measuring the ratios of the components of the whole blood and the volume of blood supplied to the separation/irradiation chamber, the intensity and duration of irradiation exposure can be regulated to result in a controlled reaction of the lymphocytes to irradiation in combination with a photoactivatable compound.

At the end of the desired period of irradiation the motor 22 is turned off to stop the rotation of the separation/irradiation chamber 14. The separated blood components flow down from the outer compartment 62 of the chamber and down the sloped bottom 26 of the chamber, where they are remixed as they collect in the blood collection well 15. The blood is pumped out of the collection well through the feed tube 13 for return to the patient. The disposable components of the system which have come into contact with body fluids are removed and disposed of, including the sep aration/irradiation chamber 14, the dynamic seal, and the shaft 9 and attached components 10-13, which are unclamped from the cover 3.

A constructed embodiment as described in FIG. 1 has been built and tested using 250 ml. of whole blood and a rotational speed of 1650 RPM. It was found that, at a rotational speed of as low as 200 RPM, blood had begun to migrate up the outer wall of the separation/irradiation chamber under the influence of centrifugal force. After the separation and irradiation process was completed, it was found that the separated blood consitiuents remixed at the bottom of the chamber due to angular deceleration and pumping as the centrifuge slowed down and came to a stop.

Figure 3:
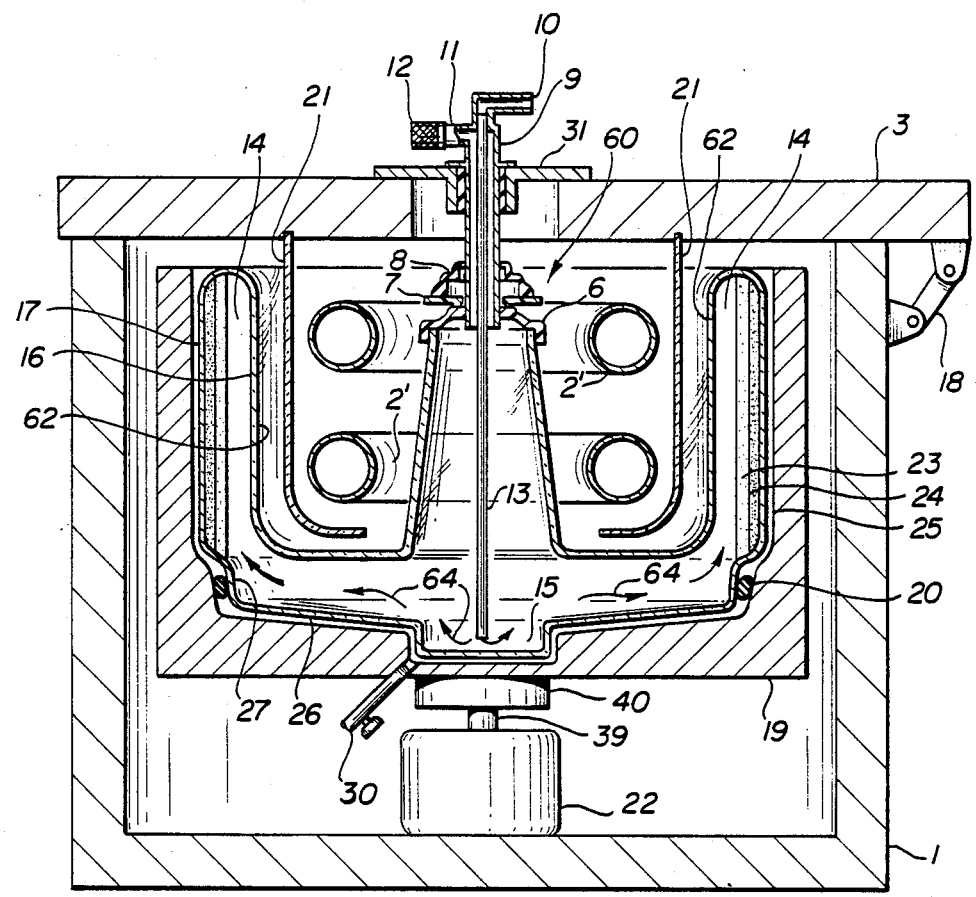
FIG. 3 is an alternate embodiment of the system of FIG. 1 utilizing a circular tube light source.

FIG. 3 illustrates a modified form of the embodiment of FIG. 1, differing in that circular U.V. bulbs 2' are in place of the U-shaped bulbs of FIG. 1. Like the embodiment of FIG. 1, the circular bulbs 2. are suitably attached to the underside of the cover 3, and are protected by the surrounding bulb cover 21 which is transparent to U.V. light.

Figure 4:
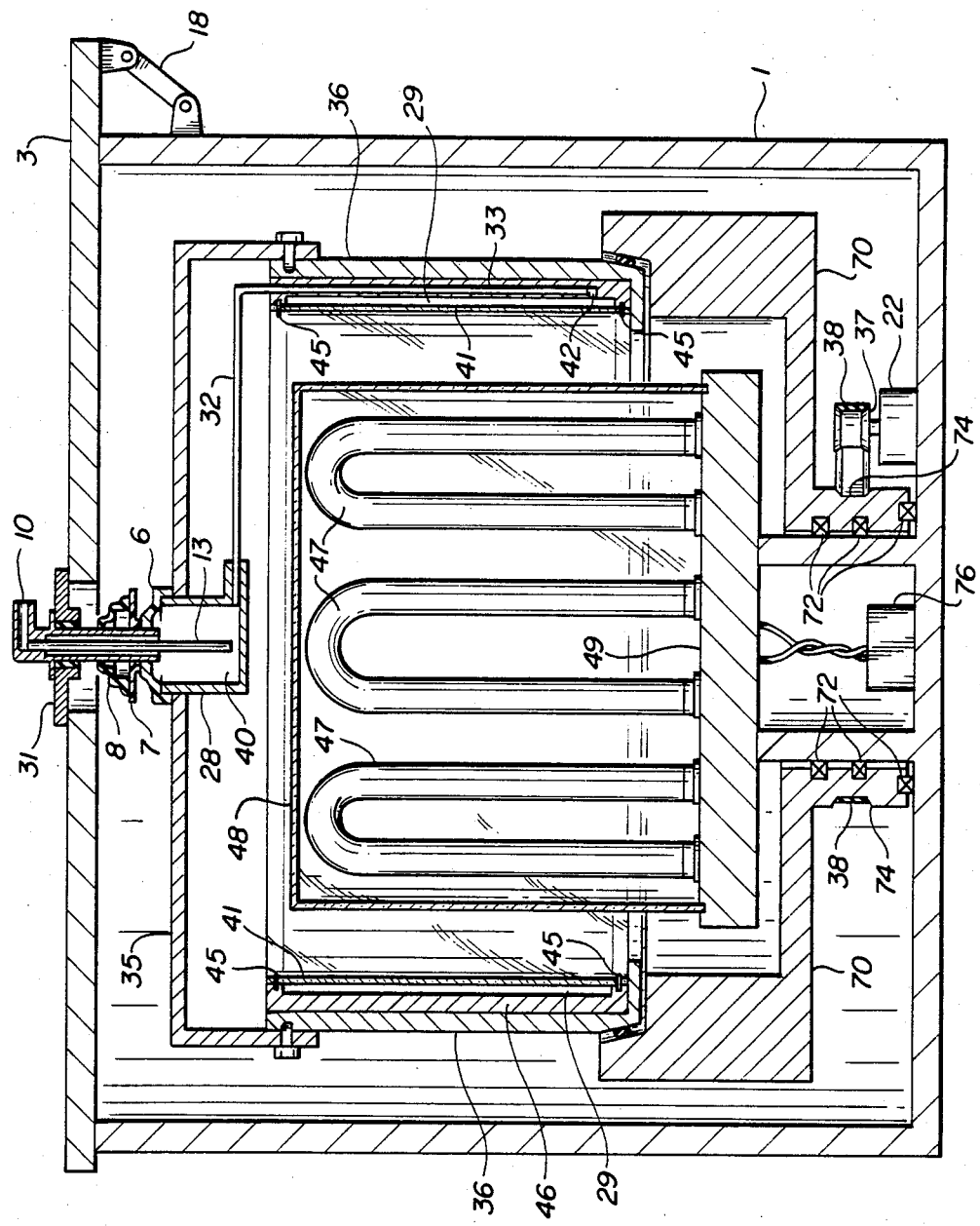
FIG. 4 illustrates a cross-sectional view of a second multicomponent fluid separation and irradiation system constructed in accordance with the principles of the present invention.

Referring now to FIG. 4, a second embodiment of a whole blood separation and irradiation device constructed in accordance with the principles of the present invention is shown. In this embodiment the stationary section of the device is substantially the same as described above, including the cover 3, the housing 1, the feed tube 13 affixed through the cover clamp 31, and the stationary component 7 of the seal with its elastic member 8. Unlike the previous embodiment, the rotatable component 6 of the rotary seal is clamped so as to enter a rotating fluid entry compartment 28 at the upper portion of the device. The feed tube 13 extends through the cover 3 to a point near the bottom of the fluid entry compartment. A support member 35 is attached between the fluid entry compartment 28 and an outer centrifuge drum 36 of the rotatable section of the device. The centrifuge drum 36 is seated in a rotating chuck 70. A groove 74 for a drive belt 38 is formed around the lower extension of the chuck 70. The drive belt 38 is located around the groove 74 and pulley 37 of the drive motor 22. The rotating chuck 70 rotates with respect to the housing by bearings 72 located between the chuck and the housing.

Located inside the centrifuge drum 36 is an array of five U-shaped U.V. bulbs 47. The bulbs 47 are mounted on a bulb mount 49 at the bottom of the device. The bulbs are surrounded by a protective bulb cover 48 which is transparent to U.V. light. The bulbs 47 are energized by a power source 76 located inside the housing.

Blood is conducted from the fluid entry compartment 28 to a separation/irradiation chamber 29 by a radial feed tube 32. The feed tube 32 is continued downward through a passageway 33 of the separation/irradiation chamber 29 and terminates at a port 42 at the bottom of the chamber. While only a single radial feed tube is shown in the embodiment of FIG. 4, it may be appreciated that a number of such tubes may radiate from the fluid entry compartment, or that blood may be conducted from the fluid entry compartment by a hollow disk-shaped member radiating outward from the fluid entry compartment. In such alternatives an array of vertical passageways would be used to conduct the blood to the bottom of the chamber 29.

Figure 5:
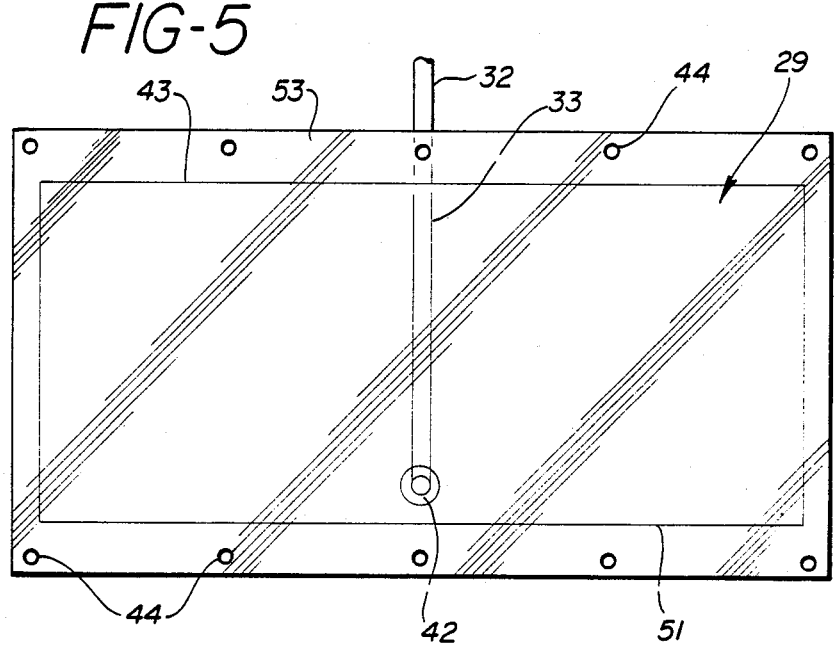
FIG. 5 is an elevational view of the fluid separation compartment of the embodiment of FIG. 4.
Figure 6:
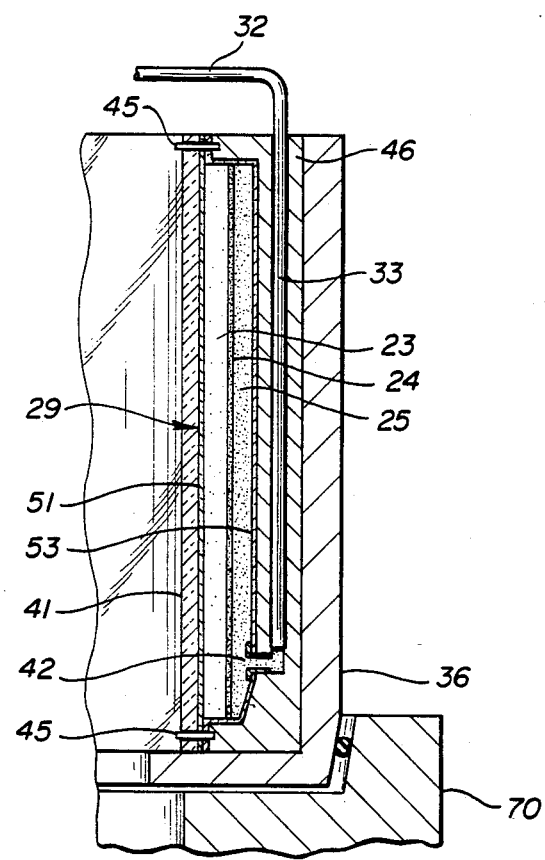
FIG. 6 is an enlarged cross-sectional view of the fluid separation compartment of the embodiment of FIG. 4.

Located inside the centrifuge drum 36 is a cylindrical separation/irradiation chamber 29, shown in an enlarged cross-section in FIG. 6 and in FIG. 5. In the latter FIGURE the cylindrical chamber has been "unrolled" to a flat shape for clarity of illustration. The chamber 29 is connected to a rigid plastic or metal support plate 46 as its outer member. Around the periphery of the support plate are a number of locating pins 45. When the chamber 29 is mounted inside the centrifuge drum 36, locating holes 44 of the chamber fit over the matching locating pins 45. The support plate 46 includes a passageway or passageways for passage of the vertical section 33 of the feed tube 32.

The disposable chamber 29 is formed of two flexible polymeric sheets 51, 53 which are transparent to U.V. light and are heat or adhesively sealed about the periphery of sheet 51 as indicated at 43 to form a bag-like compartment. As shown in FIG. 5, blood is supplied to the chamber at the inlet port 42 where the feed tube section 33 enters the chamber. The locating holes 44 are spaced around the periphery of the outer polymeric sheet 53. When the flexible chamber is mounted in the centrifuge, it is covered around its inner surface by a cylindrical supporting wall 41, which is transparent to light at the critical wavelength and contains holes which align with the locating pins 45. The supporting wall 41 prevents the development of bulging at the bottom of the flexible chamber as the centrifuge slows down and blood accumulates at the bottom of the flexible compartment.

In operation the separation/irradiation chamber 29 and the supporting wall 41 are mounted inside the centrifuge drum 36 against the support plate 46 and the radial feed tube or tubes 32 are connected to the fluid entry Compartment 28. The centrifuge drum and chuck are then rotated by the motor and its belt and pulley drive arrangement. The separation/irradiation chamber 29 is primed by pumping heparanized saline solution into the chamber as it rotates. After the chamber has been thoroughly primed with the solution the centrifuge is slowed to a rotational speed below 100 RPM (e.g., about 20 RPM) and the supply pump is reversed to pump the saline solution out of the separation/irradiation chamber. As the solution is pumped out the flexible chamber 29 collapses to its initial empty condition.

Following the priming procedure the centrifuge is accelerated to its separation speed, e.g., on the order of 1000–6000 RPM, depending upon the diameter of the chamber. Whole blood is then pumped into the separation/irradiation chamber through the feed tube 13 leading to the fluid entry compartment 28. The centrifugal forces of the rotating fluid entry compartment push the blood outward through the radial feed tube 32 where it flows down the vertical tube portion at 33 and through the port 42 to the separation/irradiation chamber 29. The chamber 29 is initially collapsed as the flexible chamber is pressed against the support plate 46 due to centrifugal force, but the flow of blood will expand the flexible chamber toward the supporting wall 41 as blood fills the chamber. The whole blood then becomes distributed in layers, as described above, against the outer wall of the rotating separation/irradiation chamber 29. U.V. light from the light source 47 will pass through the protective bulb cover 48, the supporting wall 41, the inner chamber sheet 51, and the inner plasma layer 23 to reach the lymphocytes in the buffy coat layer 24, shown most clearly in FIG. 6.

When the desired irradiation period has ended, the rotating centrifuge drum is slowed down, preferably to a speed below 50 RPM. The separated blood begins to flow downward in the chamber under the influence of gravity and the flexible sheets of the chamber collapse as blood is Pumped out of the chamber through the port 42 and tubes 13, 32 and 33. When the chamber has been emptied the flexible chamber is collapsed back to its initial position against the outer wall of the chamber. By reason of this collapsible and expandable bag-like chamber there is no need to vent air from the chamber during the filling procedure. The disposable components are removed and disposed of after use, including the separation/irradiation chamber 29, tubes 13, 32, and 33, the compartment 28, and the dynamic seal.

Figure 7:
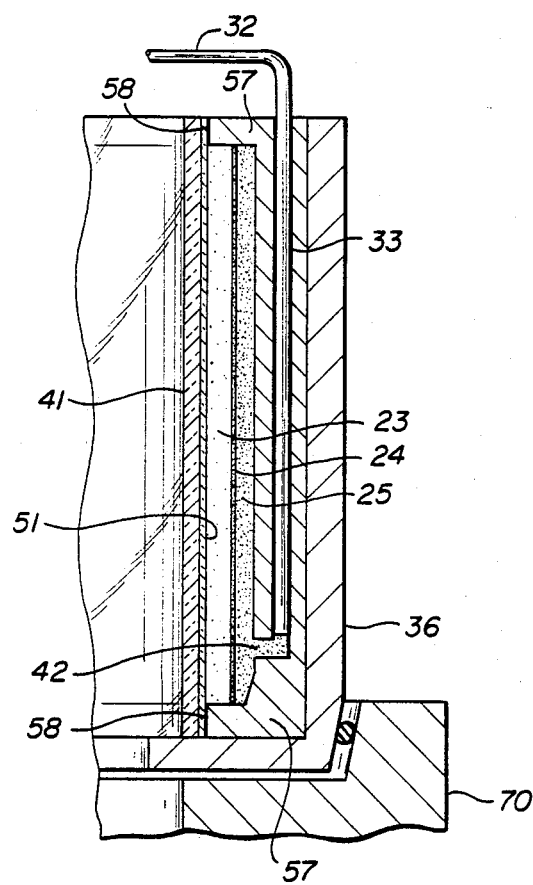
FIG. 7 is an enlarged cross-sectional view of an alternate embodiment of the fluid separation compartment of the embodiment of FIG. 4.

FIG. 7 shows an alternate embodiment of the chamber 29 of FIGS. 4–6, in which the inner cylindrical surface of the chamber 29 is formed of a sheet 51 of flexible film which is sealed about its periphery 58 to a rigid support component 57, the latter functioning as both the outer wall of the separation/irradiation chamber and the support plate 46. In this embodiment the need for a separate support plate distinct from the separation/irradiation chamber is eliminated. Overlying the flexible film inner surface of the chamber in this embodiment is the inner cylindrical supporting wall 41 which is mounted on locating pins extending from the periphery of the inner surface of the chamber Some of the polymeric material suitable for use as the support component 57, the supporting wall 41, and the flexible film 51 include polypropylene, polyethylene, ethylvinyl acetate, polyvinylchloride, and acrylic materials.

Figure 8:
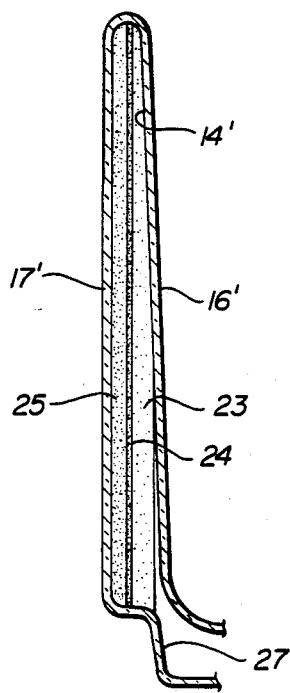
FIG. 8 is a cross-sectional view of a fluid separation compartment which is filled with a predetermined quantity of blood.

A further embodiment of a separation/irradiation chamber 14' suitable for use in the device of FIG. 1 is shown in FIG. 8 It has been found that occasional bubbling of the whole blood can cause small deposits of red blood cells to strike and adhere to the inner wall 16 of the separation/irradiation chamber 14 of FIG. 1. These small deposits of red cells can retard the transmission of light from the bulbs 2 to the separated buffy coat layer 24. The separation/irradiation chamber 14' of FIG. 8 alleviates this condition by providing a volume between the chamber walls which is substantially entirely filled with a predetermined volume of blood. The separation/irradiation chamber 14' of FIG. 8 is approximately 4 inches in height and has a controlled spacing between the inner wall 16' and the outer wall 17' which can be filled as shown in FIG. 8 by 250 ml. of blood. The space between the walls at the top of the chamber is approximately 2 mm, and at the center of the wall height the space is approximately 6 mm wide. This spacing is achieved by employing a vertical outer wall 17' and an inwardly tapering inner wall 16', which tapers away from the outer wall at an angle of approximately 2°–3°. The angular taper allows air in the chamber to be replaced by blood by migrating down the inner tapered wall and to the center of the chamber, where it is vented out through the shaft 9 and the air outlet port 11. As the separating blood fills the volume of the separation/irradiation chamber 14', the plasma layer will continually wash the inner wall 16', causing any red blood cells at the inner wall surface to detach and migrate to the outer wall under the influence of centrifugal force. Thus, there is no air gap between the inner wall 16' and the plasma layer 23, which eliminates irradiation losses due to the passage of light through the air gap and reflective losses at the surface of the plasma layer As the separation/irradiation chamber of FIG. 8 is slowed down after the separation and irradiation procedure, the inner wall of the chamber is again washed by the angular deceleration of the plasma layer as the seParation/irradiation chamber comes to a stop.

What is claimed is:

1. A system for separating and irradiating blood comprising:
   a housing;
   a rotatable member located within said housing;
   a disposable separation/irradiation chamber suitable for mounting in said rotatable member and including a vertical cylindrical outer compartment in fluid communication with an inner compartment extending between said outer compartment and the center of said chamber, and a first passageway accessing said inner compartment;
   a dynamic seal having a rotating member and a stationary member, said rotating member being connected to said inner compartment of said chamber, and said first passageway passing through said dynamic seal; and
   a source of radiant energy connected to said housing and located within said separation/irradiation chamber so at to oppose the inner wall of said outer compartment, wherein said inner wall of said outer compartment is transmissive of radiant energy of a given wavelength.

2. The separation and irradiation system of claim 1, wherein said inner compartment of said separation/irradiation chamber extends inwardly from the bottom of said outer compartment and said first passageway is connected at the center of said inner compartment.

3. The separation and irradiation system of claim 2, wherein said separation/irradiation chamber further includes a central compartment extending upward and in fluid communication with said inner compartment, said dynamic seal is connected to said central compartment, and said source of radiant energy is located between said central compartment and said inner wall of said outer compartment.

4. The separation and irradiation system of claim 3, wherein said first passageway extends through said central compartment to a point near the bottom of said inner compartment.

5. The separation and irradiation system of claim 4, further comprising a second passageway accessing said separation/irradiation chamber and extending through said dynamic seal for the passage of air out of said separation/irradiation chamber.

6. The separation and irradiation system of claim 5, wherein said first and second passageways Pass concentrically through said dynamic seal.

7. The separation and irradiation system of claim 5, wherein said housing includes an aperture passing therethrough, and further including:
   means for attaching said first and second passageways and said stationary member of said dynamic seal to said housing, whereby said passageways are accessible external to said housing.

8. The separation and irradiation system of claim 7, wherein said housing includes a housing cover containing said aperture and means for detachably affixing said passageways in said aperture.

9. The separation and irradiation system of claim 3, further including a shield attached to said housing which is transmissive of radiant energy at said given wavelength and is located between said source and said outer compartment.

10. The separation and irradiation system of claim 2, wherein said separation/irradiation chamber further includes a radial step located at the lower jointure of said inner and outer compartment surfaces.

11. The separation and irradiation system of claim 2, wherein said inner compartment includes a bottom floor which is sloped toward the center of said chamber.

12. The separation and irradiation system of claim 11, wherein said inner compartment further includes a collection well located at the center of said floor, said collection well being accessed by said first passageway.

13. The separation and irradiation system of claim 2, wherein said radiant energy source comprises a plurality of U-shaped bulbs arranged in a circular pattern in opposition to the inner wall of said outer compartment.

14. The separation and irradiation system of claim 2, wherein said radiant energy source comprises a plurality of circular shaped bulbs arranged in a vertical pattern in opposition to the inner wall of said outer compartment.

15. The separation and irradiation system of claim 1, wherein said inner compartment comprises:
   a fluid entry compartment attached to said rotatable member; and
   conduit means for fluidly connecting said fluid entry compartment and said outer compartment.

16. The separation and irradiation system of claim 15, wherein said outer compartment is collapsible.

17. The separation and irradiation system of claim 16, further comprising a rigid cylindrical member suitable for mounting inside said rotatable member for retaining said collapsible outer compartment between said rotatable member and said rigid cylindrical member. 15, wherein said outer compartment is collapsible.

18. The separation and irradiation system of claim 15, said fluid entry compartment is located at the top said separation/irradiation chamber.

19. The separation and irradiation system of claim 18, wherein said conduit means is connected between said fluid entry compartment and a point near the bottom of said outer compartment.

20. The separation and irradiation system of claim 15, wherein said housinq includes an aperture passing therethrough, and further including:
   means for attaching said first passageway and said stationary member of said dynamic seal to said housing, whereby said passageway passes through said aperture.

21. The separation and irradiation system of claim 20, wherein said housing includes a housing cover containing said aperture and means for detachably affixing said passageway in said aperture.

22. The separation and irradiation system of claim 21, further including a shield attached to said housing which is transmissive of radiant energy at said given wavelength and is located between said source and said outer compartment.

23. The separation and irradiation system of claim 22, wherein said radiant energy source comprises a plurality of U-shaped bulbs arranged in a circular pattern in opposition to the inner wall of said outer compartment.

24. The separation and irradiation system of claim 1, wherein said outer compartment further includes an outer wall which is spaced apart from said inner wall so that, when said outer compartment is rotated and filled with a predetermined quantity of blood, an air gap exists between the inner surface of said blood and said inner wall.

25. The separation and irradiation system of claim 1, wherein said outer compartment further includes an outer wall which is spaced apart from said inner wall so that, when said outer compartment is rotated and filled with a predetermined quantity of blood, the inner surface of said blood is in contact with a substantial portion of said inner wall.

26. In a system for separating and irradiating blood which includes a centrifuge drum, means for mounting a separation/irradiation chamber within said drum, and a source of radiant energy located within said drum, a disposable separation/irradiation chamber comprising:
first and second flexible sheets, at least one of which is transparent to said radiant energy, said sheets being bonded together to form an interior compartment, said interior compartment being connected to a fluid entry passageway, and including means connectable with said mounting means for mounting said compartment-forming sheets within said centrifuge drum with said transparent sheet opposing said energy source.

27. The system of claim 26, further including a rigid cylindrical member mountable within said centrifuge drum for retaining said compartment-forming sheets between said drum and said rigid cylindrical member, wherein said rigid cylindrical member is transmissive of said radiant energy.

28. of claim 27, wherein said passageway is connected near the bottom of said interior compartment.

29. The system of claim 27, wherein said mounting means comprise a plurality of pins located about the periphery of said drum, said means connectable with said mounting means comprise a plurality of holes located about the periphery of said interior compartment which align with said pins, and wherein said rigid cylindrical member includes a plurality of holes located about its periphery which align with said pins.

30. In a system for separating and irradiating blood which includes a centrifuge drum, and a source of radiant energy located within said drum, a disposable separation/irradiation chamber comprising:
a rigid outer cylindrical member;
a sheet of flexible material which is transparent to said radiant energy, said sheet being peripherally bonded inside said outer cylindrical member to form a compartment with a flexible inner wall; and
a fluid entry passageway accessing said compartment, wherein when said separation/irradiation chamber is mounted within said centrifuge drum, said transparent sheet opposes said energy source.

31. The system of claim 30, further including a rigid cylindrical member mountable within said centrifuge drum for retaining said separation/irradiation chamber between said drum and said rigid cylindrical member, wherein said rigid cylndrical member is transmissive of said radiant energy.

32. The system of claim 30, wherein said passageway is connected near the bottom of said compartment.

33. The system of claim 32, wherein said passageway accesses said compartment through said outer cylindrical member.

* * * * *